US009724270B2

(12) United States Patent
Bonnal et al.

(10) Patent No.: US 9,724,270 B2
(45) Date of Patent: Aug. 8, 2017

(54) NEEDLE FREE CONNECTOR WITH A COLLAPSIBLE RESILIENT MEMBRANE FITTING AND CORRESPONDING METHOD

(75) Inventors: Olivier Bonnal, Melsungen (DE); Juergen Fuchs, Bad Emstal (DE)

(73) Assignee: B. Braun Melsungen AG, Melsungen (DE)

( * ) Notice: Subject to any disclaimer, the term of this patent is extended or adjusted under 35 U.S.C. 154(b) by 157 days.

(21) Appl. No.: 14/236,841

(22) PCT Filed: Aug. 3, 2012

(86) PCT No.: PCT/EP2012/065306
§ 371 (c)(1), (2), (4) Date: Feb. 3, 2014

(87) PCT Pub. No.: WO2013/017698
PCT Pub. Date: Feb. 7, 2013

(65) Prior Publication Data

US 2014/0174578 A1 Jun. 26, 2014

(30) Foreign Application Priority Data

Aug. 4, 2011 (EP) .................................... 11306014

(51) Int. Cl.
*A61M 39/26* (2006.01)
*A61M 39/04* (2006.01)
(Continued)

(52) U.S. Cl.
CPC .......... *A61J 1/2096* (2013.01); *A61M 39/045* (2013.01); *A61M 39/10* (2013.01);
(Continued)

(58) Field of Classification Search
CPC .. A61M 39/26; A61M 39/045; A61M 39/267; A61M 39/268; A61M 2039/261;
(Continued)

(56) References Cited

U.S. PATENT DOCUMENTS 5,810,773 A 9/1998 Pesnicak
6,036,171 A * 3/2000 Weinheimer .......... A61M 39/26 251/149.1

(Continued)

FOREIGN PATENT DOCUMENTS

CN 1158574 A 9/1997
CN 1802183 A 7/2006

(Continued)

OTHER PUBLICATIONS

International Search Report completed Sep. 21, 2012 and mailed Nov. 21, 2012 from corresponding International Application No. PCT/EP2012/065306 filed Aug. 3, 2012 (5 pages).

(Continued)

*Primary Examiner* — Mary McManmon
*Assistant Examiner* — Hailey K Do
(74) *Attorney, Agent, or Firm* — Klein, O'Neill & Singh, LLP

(57) ABSTRACT

A needle free connector for fluid passage having a valve body with a first port; a second port; a hollow resilient membrane disposed in the valve body and having: a first end and a second end is disclosed. A flank is provided and extends between the first end and the second end fitting with the internal surface of the valve body. A slit of the first end is closed when the first end is disposed in the first port or opened when the first end is pushed into the valve body. The disclosure also proposes a drug recipient including a bottle or a bag designed to store drug and the needle free connector. The disclosure offers a needle free connector with a slitted resilient membrane having reduced priming volume.

22 Claims, 6 Drawing Sheets

(51) Int. Cl.
*A61J 1/20* (2006.01)
*A61M 39/10* (2006.01)

(52) U.S. Cl.
CPC ..... *A61M 39/26* (2013.01); *A61M 2039/1027* (2013.01); *A61M 2039/1033* (2013.01); *A61M 2039/1072* (2013.01); *A61M 2039/267* (2013.01); *Y10S 604/905* (2013.01); *Y10T 137/9029* (2015.04)

(58) Field of Classification Search
CPC ...... A61M 2039/263; Y10T 137/87957; Y10T 137/87989; Y10T 137/88054; Y10T 137/1767; F16K 7/20; F16K 15/144; F16K 15/145; F16K 15/147
See application file for complete search history.

(56) References Cited

U.S. PATENT DOCUMENTS

| | | | | |
|---|---|---|---|---|
| 6,068,011 | A | 5/2000 | Paradis | |
| 6,079,432 | A | 6/2000 | Paradis | |
| 6,541,802 | B2 * | 4/2003 | Doyle | A61M 39/26 251/149.1 |
| 6,808,161 | B1 * | 10/2004 | Hishikawa | A61M 39/045 251/149.1 |
| 7,037,302 | B2 * | 5/2006 | Vaillancourt | A61M 39/26 604/533 |
| 7,396,348 | B2 * | 7/2008 | Newton | A61M 39/26 604/256 |
| 2003/0050610 | A1 | 3/2003 | Newton et al. | |
| 2003/0098430 | A1 | 5/2003 | Leinsing et al. | |
| 2006/0111694 | A1 * | 5/2006 | Fukai | A61M 39/045 604/403 |
| 2007/0218757 | A1 | 9/2007 | Guala | |

FOREIGN PATENT DOCUMENTS

| | | | |
|---|---|---|---|
| CN | 101152594 | A | 4/2008 |
| CN | 101626792 | A | 1/2010 |
| RU | 44511 | U1 | 3/2005 |
| WO | WO 98/50106 | A1 | 11/1998 |
| WO | WO 2004/082756 | A1 | 9/2004 |
| WO | WO 2006/088858 | A2 | 8/2006 |

OTHER PUBLICATIONS

Examiner's Report on corresponding foreign application (CN Application No. 201280048844.2) from the State Intellectual Property Office dated Jun. 30, 2015.

Examiner's Report on corresponding foreign application (RU Application No. 2014108061) from the Russia Intellectual Property Office dated May 24, 2016.

Decision to Grant on corresponding foreign application (RU Application No. 2014108061) from the Russian Intellectual Property Office dated Oct. 19, 2016.

* cited by examiner

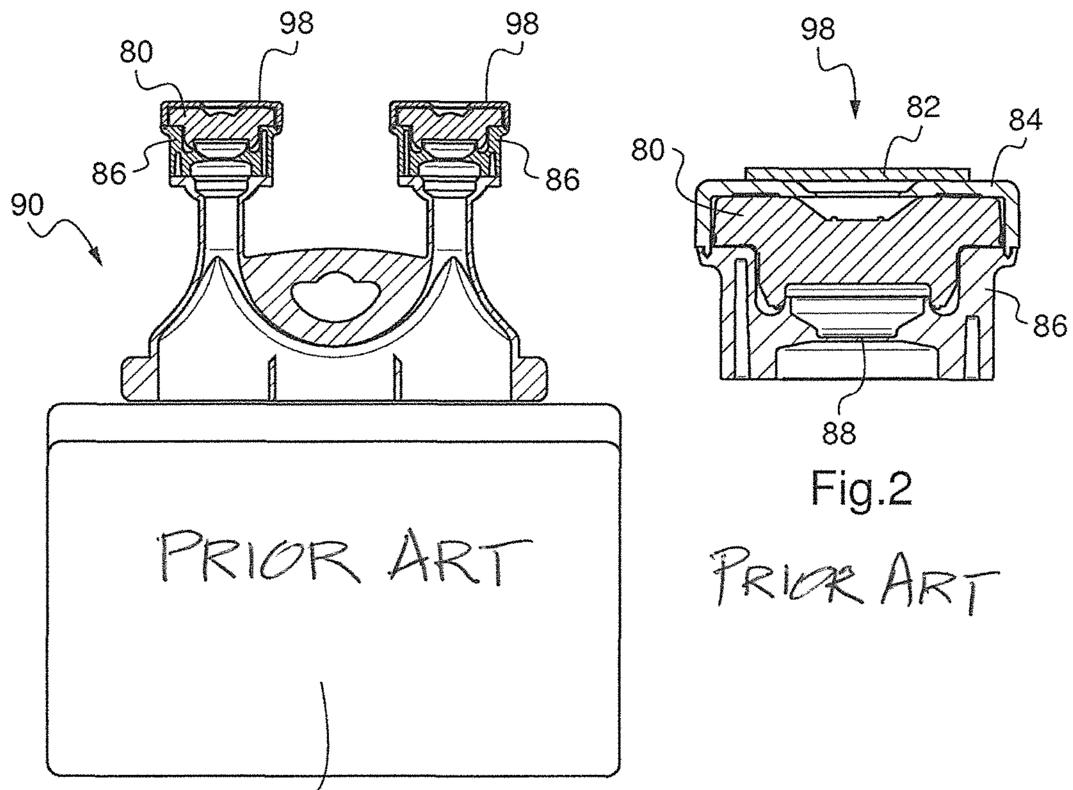
Fig.1
Fig.2
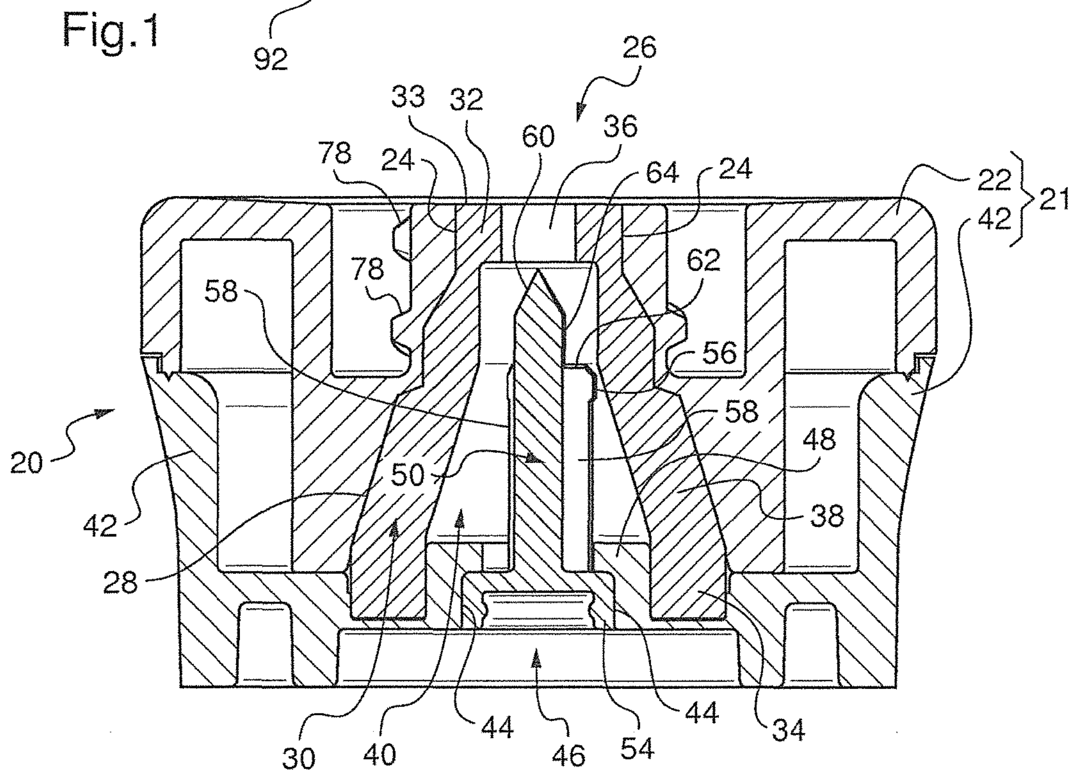
Fig.3

36
33
32
112
114
116
30
110
38
118
34

32
36
60
62
30
50
22
56
40
58
48
34
42
54
38

33
36
60
30
62
20
64
56
58
58
22
48
42
54

62
36
60
33
30
20
56
58
22
58
48
42
54

36
30
22
120
124
130
122

36
120
30
130
124
A
A 40
30
130
22
134
120
122

128
132

NEEDLE FREE CONNECTOR WITH A COLLAPSIBLE RESILIENT MEMBRANE FITTING AND CORRESPONDING METHOD

FIELD OF ART

Aspects of the present device, system, and method relate to a needle free connector for transferring fluid between a source and a receiver and more particularly directed to a device, system, and method involving a needle free connector having a hollow resilient membrane. The present device, system, and method also relate to a drug recipient comprising a bottle or a bag designed to store drug and wherein the connector is configured to access the contents stored in the bottle or bag.

BACKGROUND

Connectors and ports are widely used to inject drugs into a bottle or a plastic bag filled with fluids. These injection connectors allow the drug to be diluted with a solution before administering the same to a patient. Connector ports are also used with IV lines or tubing as a means for vascular access.

When injecting drugs into a bag, it is known to use a port with an elastomeric stopper. Before the first activation or use, the elastomeric stopper may be devoid of any hole or opening. The injection of drugs is typically implemented by using a syringe with a needle and filled with the drugs to pierce the elastomeric stopper and then discharging the drugs through the elastomeric stopper and into the bag. The elastomeric stopper may be resealable in order to avoid leak through the stopper after removal of the needle of the syringe, typically by compressive resilient force.

FIG. 1 shows a cross sectional view of a bag 90 storing a medical solution 92 before administering the solution to a patient. The medical solution 92 can be accessible through two known access ports 98, such as an administrative port and an additive port. The known ports are each typically equipped with an elastomeric stopper 80 disposed on a base port 86. The base port 86 may be sealed directly on the bag 90 made of plastic or thermoplastic films.

FIG. 2 shows an enlarged cross sectional view of one of the access port 98 according to FIG. 1. The known port 98 further comprises a resealable cap 84 covered by a tamper-proof cover 82. The tamper-proof cover 82 may correspond to a peelable aluminium foil sealed on the resealable cap 84. In order to inject into or remove drug from the bag 90, the elastomeric stopper 80 is designed to be punctured by a needle of a syringe or by the needle of an intravenous line after removal of the peelable cap 82. The port 98 further includes a pierceable membrane 88 integral with the base port 86. This pierceable membrane 88 forms an aging resistant barrier between the stored medical solution and the elastomeric stopper 80. This membrane is irreversibly broken upon first activation of the port, when for the first time a needle punctures the membrane 88 together with the elastomeric stopper 80.

The known port with puncturable elastomeric stopper necessitates the use of a needle to inject or withdraw drugs from the bag. Nowadays, the use of a needle is less desirable as it presents an accidental puncture hazard during manipulation by a health worker.

US publication No. 2003/0141477 A1 proposes a medical valve that avoids the use of needle in the transmission and delivery of fluid products to patients in a sterile environment. This valve is formed with a slitted hollow resilient membrane, the slit of the membrane being closed or opened depending on the insertion of a tip of a Luer lock connector in the valve. Once the slit is opened, a fluid passage is form trough the resilient membrane allowing the injection or withdrawal of drugs through the valve. Thus this valve satisfies the requirement of a needle free use, yet many other requirements are to be fulfilled. Among the many requirements that the medical valve of US publication No. 2003/0141477 A1 tries to satisfy, this valves fails to disclose a minimizing of the priming volume.

SUMMARY

Accordingly, the present aims to include a needle free connector with a slitted resilient membrane having reduced priming volume. It will be appreciated that the device, system and method involving connectors disclosed herein provide other features and benefits.

This object is achieved with a needle free connector for fluid passage, comprising:

- a valve body comprising:
  - a first port;
  - a second port; and
  - an internal surface that extends between the first port and the second port and defining a valve body cavity;
- a hollow resilient membrane disposed in the valve body and having:
- a first end and a second end between which the resilient membrane longitudinally extends, the second end having a through hole that opens into the second port;
- a flank extending between the first end and the second end and located in the valve body cavity of the valve body and fitting with the internal surface, the flank defining an internal cavity of the hollow resilient membrane, the internal cavity extending longitudinally from a through slit located at the first end to the through hole of the second end; the slit of the first end being:
- closed when the first end is disposed in the first port so as to occlude the first port or
- opened when the first end is pushed into the valve body so as to create a fluid passage through the first end and the cavity up to the second end.

Preferred embodiments are defined in the dependent claims. The invention further proposes that:

- the first end of the hollow resilient membrane disposed in the first port forms a flat swabbable surface.
- the first port is shaped so as to connect with a male luer lock syringe.
- the first end of the membrane is able to be pushed towards the second port by insertion of a syringe tip into the first port; and the resilient membrane being formed so as to urge the first end of the membrane back into the first port after removal of the syringe tip from the first port.
- the internal volume of the longitudinal cavity between the first end and the second end forms entirely a fluid passage.
- the needle free connector comprises a stem disposed within the cavity and wherein the second port being occluded until a first activation of the second port during which the stem is pushed relative to the second port, together with the pushing of the first end of the membrane towards the second end, so as to un-occlude the second port.
- the stem has a base portion tight fitted in second port until the first activation of the second port.
- the stem has a base portion that occludes the second port and is integral with a valve body part of a valve body through a frangible portion until the first activation of the second port, the frangible portion being broken upon first activation of the second port.

the second port is occluded by a pierceable wall, the stem having a sharpened end in the vicinity of the second port, the sharpened end piercing the pierceable wall upon first activation of the second port.

the stem have longitudinal ribs forming fluid channels to keep the fluid passage between the stem and the flank of the membrane un-occluded upon activation of the first port.

upon activation of the first port, the slit of the first end passes around the stem towards the second end.

the stem has a shoulder in the vicinity of the first port, designed to abut a tip of a syringe inserted in the first port upon first activation of the first port, so as to transmit the movement of the inserted tip of the syringe to the stem and activate the second port.

the stem has a narrowing in the vicinity of the first port, designed to enter an inner channel of a tip of a syringe inserted in the first port.

The invention also proposes a drug recipient comprising a bottle or a bag designed to store drug, and the previous needle free connector so as to inject and/or withdraw fluid from the drug recipient.

The invention further proposes an assembly for fluid passage comprising the previous needle free connector, the assembly being a stopcock or a withdrawal and injection spike device comprising a spike for puncturing a drug vial.

Aspects of the present connector may be practice by reducing the priming space in the internal cavity of the membrane. This can be carried out by providing a free space between the exterior surface of the membrane and the interior surface of the valve body to be I% or less of the volume of the internal cavity of the membrane.

A further aspect of the present connector is a provision for a stem to facilitate opening a slit on the membrane.

The stem may also be employed to guide movement of the membrane.

A still further aspect of the present connector is provision for sealing a second port to isolate the membrane from fluids located inside a container or bag. The isolation may be accomplished through an enlarged stem base in fluid tight arrangement with an annular space at the second port.

Alternatively, a pierceable membrane may be incorporated with a lower valve body portion to be pierece unocclude the second port.

BRIEF DESCRIPTION OF THE DRAWINGS

Further features and advantages of the device, system, and method will appear from the following description of embodiments of the invention, given as non-limiting examples, with reference to the accompanying drawings listed hereunder.

FIG. 1 shows a cross sectional view of a generic prior art bag storing a medical solution before administration to a patient;

FIG. 2 shows an enlarged view of one access port of the generic prior art bag according to FIG. 1;

FIG. 3 shows a cross sectional view of a connector according to a proposed embodiment;

DETAILED DESCRIPTION

Figure 4:
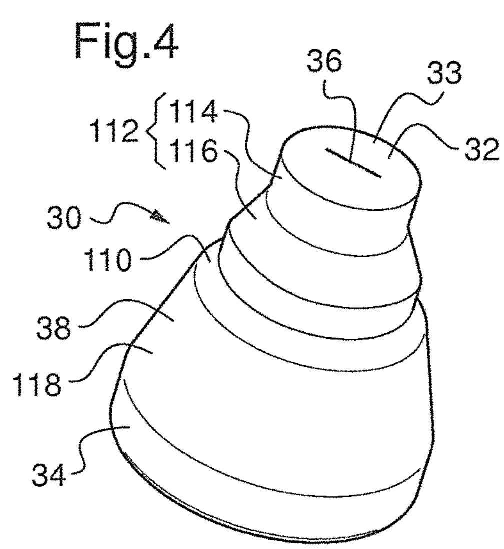
FIG. 4 shows a perspective view of a conical hollow resilient membrane being a part of the connector according to FIG. 3.

The detailed description set forth below in connection with the appended drawings is intended as a description of the presently preferred embodiments of connectors provided in accordance with aspects of the present device, system, and method and is not intended to represent the only forms in which the disclosed connectors may be constructed or utilized. The description sets forth the features and the steps for constructing and using the connectors in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

The disclosed device, system, and method involve a needle free connector for fluid passage comprising a valve body and a resilient membrane. The valve body comprises a first hole or opening delimited by a first annular space. The first hole forms a first port. Similarly the valve body comprises a second hole or opening delimited by a second annular space. This second hole forms a second port. The resilient membrane comprises a first end and a second end. The second end is hollow. Indeed the second end has a through hole, disposed to open in the second port inside the valve body. The second end of the resilient membrane may be completely or entirely hollow or alternatively only partially hollow, such as including a flange, a rib, a fin, or other surface features for mounting or engaging the resilient member within the valve body. In one embodiment, the second end is larger in diameter than the first end.

The first end of the membrane includes a through slit. The slit may be linear or partially undulating along a radial direction and may be partially opened or completely closed even when not bounded by the first port, such as when free standing outside of the valve body. When in used inside the valve body, the slit of the membrane is closed or opened depending on the disposition of the first end within the valve body. Depending on whether the slit is closed or opened, the first port of the valve body is similarly closed or opened. When the first end is disposed at the first port in a first position, the first end occludes the first port notably by closing the slit. The first position may also be referred to as a closed position. The slit is closed due to the relative dimensions of the first port and the size of the membrane at the first end. The first port is closed by not permitting any fluid to flow in or out of the valve body through the slit.

When the first end of the membrane is moved away from the first port and closer to the second end and the second port within the valve body, the slit opens and the membrane is in a second position, or open position. The first end, when disposed in the first port, may be moved closer to the second end when the first end is pushed into the valve body, such as by a tip of a syringe. The second end of the membrane is preferably fixed in the valve body so that when the first end is pushed into the valve body, the membrane undergoes a longitudinal compression. The longitudinal compression of the membrane is somewhat similar to crushing a soda can along a longitudinal direction. In one embodiment, the interior and exterior surfaces of the membrane are smooth whereas in other embodiment, the interior surface may have at least one indentation or groove, such as an annular indentation, to cause buckling at the predetermined position of the at least one indentation or groove. The pushing of the first end further into the valve body corresponds to pushing the first end towards the second port. Again, this could be done by inserting a tip of a syringe into the first port. The opening of the slit establishes fluid communication between the valve and the syringe and forms a fluid passage through the first end. Viewed another way, the pushing of the first end further into the valve body corresponds to an activation of the first port of the connector.

The resilient membrane further comprises a hollow interior with a longitudinal cavity. The resilient membrane extends longitudinally from the first end to the second end with the hollow cavity similarly extending in the same direction. As used herein, the longitudinal direction corresponds to the principal direction of extension of the hollow resilient membrane and also to the principal direction of extension of the cavity formed by the hollow resilient membrane, both of these principal directions being collinear. Consequently, the cavity is delimited longitudinally on one side by the first end and on the other side by the second end. The longitudinal cavity opens into the hollow second end, i.e. in its through hole, and extends in the slit through the first end. When the slit opens, the fluid passage formed through the first end extends through the longitudinal cavity and to the second end.

The membrane further comprises a flank or membrane body, which surrounds and defines the internal cavity. In one embodiment, the flank of the membrane fits with the internal surface of the valve body, between the first and second ports. In others words, the disposition of the membrane in the valve body imply the absence of free space around the external side of the flank of the membrane. Said differently, the exterior surface of the membrane contacts the interior valve body surface all along the flank. As a consequence, the flank of the membrane is outwardly delimited by the valve body so that during activation or opening of the first port, the pushing of the first end towards the second end can only induce deformation of the flank of the resilient membrane inwardly into the cavity. Thus the internal volume of the cavity is reduced, as opposed to increase by having an expending cavity, when drug is injected or withdrawn through the connector. The reduction of the internal volume of the cavity induces a reduction of the priming volume for the proposed connector in comparison to the prior art and notably to the valve disclosed in US publication No. 2003/0141477 A1.

The reduction of the priming volume is advantageous due to the allowed diminution of the lost drugs, which stay in the connector during injection and/or withdrawal. In accordance with an embodiment of the present method, a drug recipient, e.g., a mixing recipient, is provided comprising a bottle or a bag designed to store drug. This drug recipient is provided with the above proposed needle free connector. The proposed needle free connector allows the injection and/or withdrawal of fluids from the drug recipient. The result of a reduced priming volume for the needle free connector induces advantages for the drug recipient. Indeed, when the proposed connector is used to inject drug in the drug recipient, the reduction of the priming volume decreases the amount of drugs that remain unmixed within the connector. This is all the more advantageous when the same port is used later for withdrawing fluids from the drug recipient. The amount of unmixed drugs among the withdrawn drugs being thus limited. With consideration that certain administered drugs can have relatively small dosages, in the order of 0.05 mg/5 mL, even a small reduction in unmixed drugs can contribute to overall greater treatment and care of the patient.

With reference now to FIG. 3, a cross sectional view of the connector 20 according to aspects of the present device, system, and method is shown. This figure shows the connector comprising the valve body 21 retaining a membrane. In the embodiment shown, the valve body 21 is formed of two parts: an upper body part 22 and a lower body part 42. These two parts 22, 42 are attached together to form an enclosure defining a valve body cavity 23 for the membrane. In one example, the two parts 22, 42 are ultrasonically welded and/or glued, and/or fixed one to another by any other means being acceptable alternatives. The inner cavity 23 is defined by the internal surface 28 of the valve body 21.

The inner valve body cavity 23 is configured to receive the resilient membrane 30 with the flank 38 of the membrane 30 fitting against the internal surface 28 of the valve body 21. In one example, the flank 38 contacts the interior surface 28 of the valve body 21. However, it is possible to have a small, minimized gap, between all or parts of the flank 38 and the interior surface 28 of the valve body 21, such as due to manufacturing tolerance, or the membrane shifting. In one embodiment, the flank 38 defines an interior membrane cavity 40 having a volume X. The gap or space between the exterior surface of the flank 38 and the interior surface 28 of the valve body 21 totals about 15% or less of the volume X of the membrane cavity 40. The gap space may have a volume Y. In one specific embodiment, volume Y is about 7% or less of volume X. More preferably, volume Y is less than 2% of volume X and even more preferably less than 1%. The small volume Y implies that the exterior surface of the flank contacts the interior surface of the valve body essentially or totally along the exterior surface of the membrane. This arrangement is configured to outwardly delimit movement of the flank 38 when activating the connector. As previously described, by restriction movement of the membrane so that it moves inwardly during activation, the internal volume of the cavity 40 is reduced, as opposed to increase. The decreasing internal cavity volume as opposed to expanding cavity volume minimizes space for potential unmixing of drugs during administration. Thus, aspect of the present method is understood to include the steps of inserting a syringe into the connector comprising a membrane, discharging fluids from the syringe, and whereby a priming space defined by an interior cavity of the membrane is decreased during the discharging step. Another aspect of the present disclosure is a method for decreasing a priming space by fitting a membrane to a connector housing and delimiting outward movement of the membrane. In one embodiment, a gap between the connector housing and the membrane is 1% or less of the volume defined by the interior cavity of the membrane. In a specific embodiment, the priming space is minimized by decreasing the interior cavity of the membrane when activating the connector to be smaller than the same space when not activated.

FIG. 4 shows a perspective view of the hollow resilient membrane 30 of FIG. 3 outside of the valve body 21. As shown in FIG. 4, the membrane 30 has a generally conical shape with distinct external surfaces 110. The membrane 30 is divided into an upper membrane section 112, which includes a membrane head 114 and a membrane shoulder 116, and a lower membrane section 118, which is shown with a generally frustoconical shaped skirt. In another embodiment, the membrane 30 has a smooth exterior contour with fewer or without any distinct external surface features when compared to the FIG. 4 embodiment. In other embodiments, the lower membrane section 118 is shaped with a generally cylindrical body, as further discussed below.

Referring again to FIG. 3, the first end 32 of the membrane 30 is disposed in the first annular space 24 of the first port 26, i.e. into the first port 26. The cross sectional view shows the slit 36 along a plane in which the slit extends. The slit 36 is shown in a closed position due to the fact that the first end 32 is disposed in the annular space of the first port 26. As shown, the connector body 21 incorporates internal surface features to match the external surfaces 110 of the membrane 30 to embody a corresponding form fitting fit with the membrane. Similarly, the connector body 21 incorporates an enlarged cavity portion to accommodate the lower membrane section 118 in a form fitting configuration. The second end 34 of the membrane may be located between the upper and lower body portions 22, 42 to fixedly secure the membrane within the connector body. However, since the membrane is confined with the connector body cavity, the membrane can be retained therein without fixing or anchoring the second end 34. In both cases, the through hole of the second end 34 opens in the second port 46.

As illustrated, the first port 26 is advantageously shaped so as to connect with a male luer lock syringe or a male luer connector, such as to an administrative set. This connection is preferably obtained by inserting the tip of the syringe through the first port 26, which pushes on the first end 32 of the membrane 30 to move the first end towards the second port 46. The tip of such a syringe is devoid of any needle to prevent unintended injuries with needle. Accordingly the size of the tip of the syringe and the corresponding size of the first annular space 24 are relatively larger than the diameter of an injection needle. After activation of the first port, the luer lock syringe tip may be removed from the first port to disconnect the luer lock syringe. The resilient membrane 30 is preferably formed so as to urge the first end 32 of the membrane back into the annular space 24 of the first port 26. Thus, after removal of the syringe tip, the first port is automatically closed. This automatic closing of the first port limits or prevents bacteria from entering and cultivating inside the connector after disconnection of the syringe and prevents drugs from leaking out of the connector after disconnection, which contributes to the overall safety of the healthcare worker, notably when the drug is a cytotoxic fluid that can be harmful to the skin upon contact. To facilitate connection, external threads 78 are provided at the first port 26 for threaded engagement with the male luer lock syringe. In some embodiment, a simple luer slip is provided on the connector for engaging the tip of the syringe without the need for threaded engagement.

Thus, as understood from the present disclosure, aspects of the present device includes a connector comprising a valve body having an interior wall surface defining an interior valve body cavity, a first port, and a second port. A membrane is disposed in the interior valve body cavity comprising an exterior surface and an interior surface defining a membrane cavity having a volume X. Wherein the volumetric space between the interior wall surface of the valve body and the exterior surface of the membrane is Y and wherein Y is 5% or less of X. In another embodiment, Y is less than 1% of X. Another feature of the connector is a provision for delimiting membrane movement to inwardly contracting movement to decrease the priming volume of the membrane cavity upon activation of the connector.

Yet another feature of the present device, system and method is a provision for incorporating antimicrobial compositions into the membrane, the housing, or both the membrane and the housing. Antimicrobial agents are provided to control or combat bacterial contamination inside the connector, such as for reducing the amount of biofilm formation. Antimicrobial agents useable with the components of the present connector include silver, gold, platinum, copper, and zinc. Antimicrobial metal compounds used herein include oxides and salts of preferably silver and gold, for example: silver acetate, silver benzoate, silver carbonate, silver citrate, silver chloride, silver iodide, silver nitrate, silver oxide, silver sulfa diazine, silver sulphate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds or combinations of physiological, antimicrobial metal compounds may be used. Still alternatively, a thin antimicrobial agent may be deposited over a wall surface of the various connector components as disclosed in U.S. Pat. No. 5,782,808 to Folden.

Although the connector 20 is operational as described above, according to another embodiment a stem 50 is incorporated and disposed within the cavity 40 of the membrane 30. The stem is disposed between the first and second ports 26 and 46. The stem 50 is not needed or required to permit opening and closing the slit 36 in the manner described above. When incorporated, as further discussed below, the stem 50 is configured to open a fluid path between the interior cavity of the connector, more specifically the interior cavity of the membrane, and the contents of the container or bag. Before the first activation of the membrane and of the stern, the fluids and the membrane are isolated from one another.

With reference again to FIG. 3, the stem 50 facilitates the activation of the second port 46 as well as the activation of the first port 26. In others words, the stem 50 may contribute to the creation of a fluid passage through the second port 46 and of a fluid passage through the first port 26. Further, the stem 50 enables fluid communication between the first port 26 and the second port 46.

To activate the first port 26 of the connector having the stem, the stem, 50 may present an end 60 in the vicinity of the first port 26. This end 60 of the stem comprises a sharp structure that helps to open the slit 36 when the first end 32 of the membrane 30 is pushed towards the second port 46, i.e., during activation of the first port 26. The sharp end 60 of the stem 50 is provided to enlarge the slit 36 so that the slit 36 of the first end 32 passes around, at least in part, the stem 50 as the first end moves towards the second end 34 when activating the connector. In an alternative embodiment, illustrated in FIG. 5, the end 60 of the stem 50 presents a flat or blunt form, which is less sharp or pointed than the sharp end 60. In use, when the first end 32 is pushed by a medical implement, such as a syringe, and moves out of the annular space 24 of the first port, the slit 36 may open without the aid of the sharp end 60 of the stem. In another embodiment, the end 60 of the stem is smaller than the nominal diameter of the stem but not as sharp as shown in FIG. 3.

Figure 5:
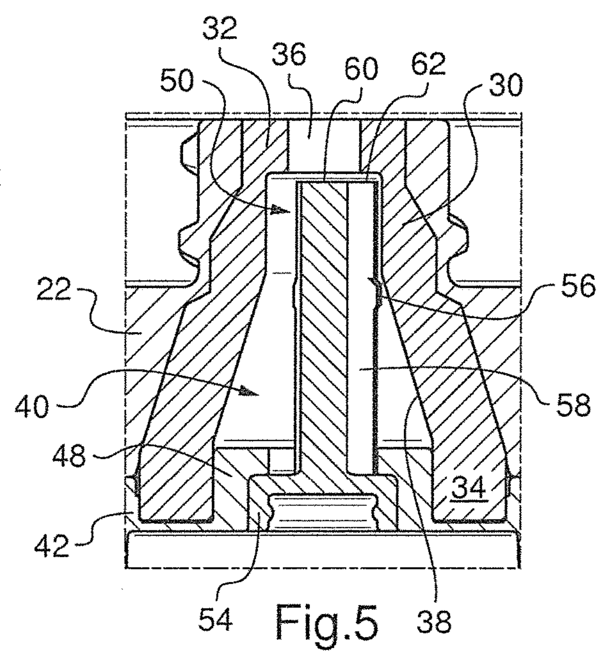
FIG. 5 shows a cross sectional view of a connector according to another proposed embodiment having the hollow resilient membrane according to FIG. 4.
Figure 6:
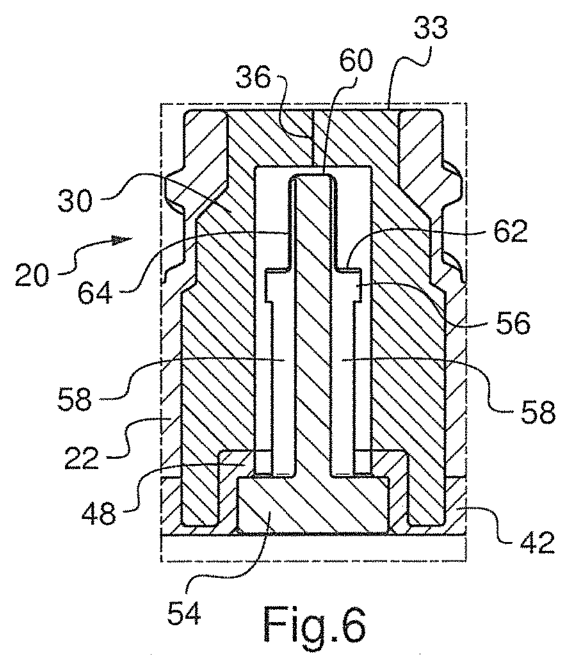
FIG. 6 shows a cross sectional view of a connector according to another proposed embodiment having a cylindrical hollow resilient membrane.

FIG. 6 shows a cross sectional view of the connector 20 provided in accordance with another aspect of the present device, system, and method. The connector 20, here also, comprises a stem 50 with an end 60 having a flat or blunt form. However, compared to the embodiment illustrated in FIG. 5, the stem 50 of FIG. 6 presents a narrowing 64 in the vicinity of the first port 26. The narrowing section 64 is generally constant as it extends towards the blunt end 60. The provision of the narrowing section may be independent from the form of the end 60, flat or sharp. Indeed in the embodiment of FIG. 3, the stem 50 also presents a narrowing portion 64, which has tapering dimensions and differs from the constant nominal diameter. The narrowing portion 64 of the stem 50 is designed to enter an inner channel of a syringe tip inserted in the first port 26 to open the connector 160. This narrowing portion 64 of the stem contributes, as well as the sharp form of the end 60, to the progressive enlargement of the slit 36 around the stem 50 when the first port is activated.

While the narrowing portion 64 entering the inner channel of the syringe tip assist in opening the slit during the connector activation, the narrowing portion may limit or partially occlude part of the fluid passage through the first port 26. In contrast, as shown in FIG. 5, the absence of the narrowing portion on the stem 50 allows a greater fluid passage for the injection or withdrawal of fluids with the syringe. The stem 50 of FIG. 5, although does not project into the inner channel of the syringe, provides a resistance to facilitate, at least to some degree, the opening of the slit, for example when the upper surface with the slit is trapped between the syringe and the flat end. Whether a narrowing section on a stem is incorporated may thus depend on the designer's choice for configuring the connector to have a slit 36 that can readily open upon activation of the first port 26 versus a connector with a greater fluid passage through the first port 26. Such choice is further linked to the material selection for the membrane 30, and in particular to its elasticity. For example, the material for the membrane could be an elastomer, typically silicon or a material having similar elasticity as silicon, to facilitate the enlargement of the slit 36 and therefore facilitate the activation of the first port 26. Thus, as readily understood, aspects of the present device, system, and method include a connector having (1) a stem for facilitating slit opening of the membrane, (2) a stem having a blunt end with flow channels or paths to optimize fluid flow through the first port, (3) a stem-less membrane for maximum flow path, and (4) a stem in combination with a membrane with provisions for both slit opening and fluid flow.

In another exemplary embodiment, the membrane is made from a thermoplastic material (TPE). The TPE may be from a copolyamide (COPA) family of thermoplastic elastomers. In an embodiment, the COPA is copolyamide thermoplastic elastomer having a commercial trade name PEBAX®. However, other TPEs may also be used to make the membrane 30, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics.

Figure 7:
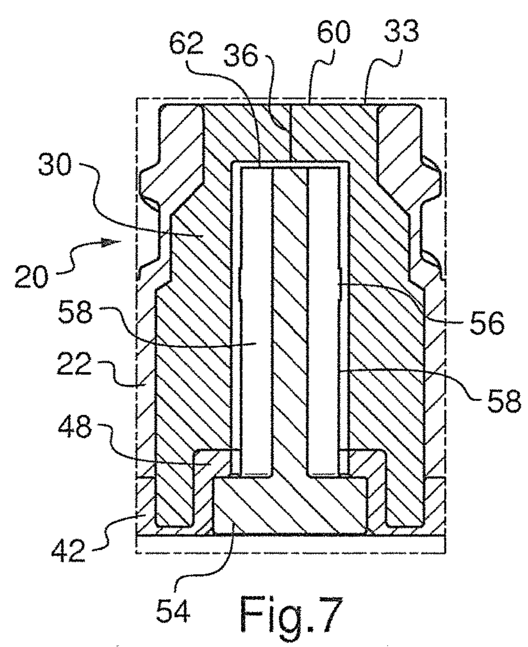
FIG. 7 shows a cross sectional view of a connector according to another proposed embodiment having a cylindrical hollow resilient membrane.

The stem 50 may have longitudinal ribs, channels or passages for fluid flow. In one embodiment, the stem 50 has three longitudinal ribs 58. The ribs may embody outwardly extending structures or indentations formed in the stem to permit fluid flow through parts of the indentations or between extending structures and other parts of the stem. In other words, the ribs provide sections of non-uniform contour to create gaps for fluid flow space. In other embodiments, there are fewer than three or more than three longitudinal ribs. These longitudinal ribs 58 serve to form fluid channels for fluid passage between the stem 50 and the interior surface of the flank 38 of the membrane 30 upon activation of the first port. The longitudinal ribs 58 are configured to limit inward deformation of the membrane 30 against the stem and sealing off fluid space between the stem and the interior wall surface of the flank. In the embodiment shown in FIG. 3, the ribs 58 may extend along the stem 50 from the end 60 (not shown), i.e., at the tip, so as to assure a fluid passage along the stem 50 as soon as the slit 36 is opened by the sharpened end 60. Embodiments shown in FIGS. 3 and 5 depict the resilient hollow membrane 30 with a conical shape. Alternatively, the resilient hollow membrane 30 may embody a cylindrical shape. FIG. 6 shows a cross sectional view of the connector 20 having a cylindrical hollow resilient membrane 30 along the middle to lower section of the membrane 118. FIG. 7 shows a cross sectional view of another embodiment of the connector 20 having a cylindrical hollow resilient membrane 30. The cylindrical shape of the hollow membrane 30 provides reduced priming volume for the proposed connector 20 by collapsing inwardly into the membrane cavity 40. The embodiment of FIG. 7 differs from the embodiment of FIG. 6 in that the stem 50 of FIG. 7 does not present a narrowing in the vicinity of the first port 26. The stem 50 of FIG. 7 is thus the same as the stem 50 of FIG. 5. However, the cross sectional view of FIG. 7 is in a plane perpendicular to the plane of the cross sectional view of FIG. 5.

The stem 50 may also regulate fluid flow through the second port 46. The connectors of FIGS. 3, 5, 6 and 7 incorporate sterns 50 that arc longitudinally movable to open fluid passages through the respective second ports. This feature is configured to separate the membrane 30 from the fluids contained inside the bag or container, such as during storage or shipment, until the stem is activated. In one embodiment, the stem, or at least part of the stem, is provided with an axially or longitudinally movable base. The base is configured to seal against the annular space at the second port 46 to occlude the second port. This occlusion is provided until the first activation of the second port 46, as further discussed below.

In one embodiment, the occlusion of the second port 46 is induced by a base portion 54 of the stem 50. This base portion 54 is snugly fitted in the annular space of the second port 46 until the first activation of the second port 46. The fit between the base portion 54 and the annular space is fluid tight so that fluids inside the container or bag cannot enter into the membrane cavity 40. When activating the second port 46 for the first time, the stem 50 is pushed at the end 60, directly or indirectly, by a medical implement, which translate the base in the same direction of the exerted force to separate the base from the annular space of the second port 46. The pushing of the stem releases the base portion 54 from the second port 46, which results in un-occluding the second port 46. Once the stem 50 has been released from the second port 46, i.e. after the first activation of the second port 46, the second port 46 remains permanently opened to provide a fluid passage through the second port 46. In an alternative embodiment, the stem could be made of two or more parts or components. According to an embodiment of the multi-part stern, at least one part of the stem is stationary while another part moves axially relative to the stationary part to provide a fluid pathway through the second port 46. The moveable stem part can be moved by a syringe tip or other medical implement to move relative to the stationary stem part.

As illustrated in FIGS. 3, 5, 6 and 7, the stem 50 advantageously presents a stop 56 designed to limit the extent of movement of the stem 50 away from the second port and further into the container or bag when the second port 46 is activated. The stop 56 may take the form of one or more radial pins extending from the center of the stem 50. The stop 56 is configured to abut against a well 48 formed around the second hole or annular space 44 of the second port. The well 48, as illustrated in FIGS. 3, 5, 6 and 7, may be formed integrally with the lower part 42 of the valve body. The well 48 also serves as a guide for guiding the stem 50 through the second port as the stem 50 is pushed during activation. In one embodiment, the stop is positioned on one or more ribs 58 of the stem 50.

The first activation of the second port 46 may be facilitated when the stem 50 presents at least a shoulder or stem end in the vicinity of the first port 26 to be used as leverage to move the stem. The shoulder can embody different configurations. FIGS. 3, 5, 6 and 7 depict different options for incorporating a shoulder 62 with the stem 50. Each shoulder 62 is designed to abut and be pushed by a tip end of a syringe tip. For example, when the syringe is inserted into the first port, it compresses the membrane and eventually abuts and pushes the shoulder to axially displace the stem further into the connector body to separate the base from the annular space of the second port. The abutment transfer movement of the syringe tip to the stem resulting in the activation of the second port 46. In others words, the first activation of the first port 26 results in the first activation of the second port 46 due to the transfer of movement of the syringe tip to the stem 50. In one embodiment, this transmission is facilitated by the provision of a shoulder 62 on the stem 50. Accordingly, the first activation of the connector corresponds to the first activation of the first port 26 together with the first activation of the second port 46.

By initially occluding the second port before the first activation, the stored drugs are separated from and do not contact the elastomeric membrane 30. The elastomeric properties of the membrane 30 may present a potential weakness when it comes to shelf-life of the drug or other medical liquid and of the membrane. Thus, by providing a base portion 54 of the stern 50 and the lower part 42 of the valve body with material or materials that are less elastic but more impervious to drug seepage or migration, the shelf-life of the container and of the drugs are increased. In others words, the material of the stem 50 and of the lower part 42 can be selected to be more compatible with the drugs than the resilient material of the membrane 30 in terms of shelf-life.

Additionally, the initial isolation of the second port and the fluids contained inside the bag or container contributes to improved air tightness when comparing the first activation against subsequent connector activations. As is readily understood, after the first activation, the membrane 30 alone isolates the drug from the exterior air. However, since the membrane is typically made from an elastomeric material, it can experience gas permeability and degrade. On the contrary before activation of the membrane, the stored drugs are isolated from the exterior and from the membrane by the base portion 54 of the stem 50 and the lower part 42 of the valve body, which may be made from less gas permeable material than elastomer material used to make the membrane 30. For example, the stem and the housing may be made from a plastic and coated with an oxygen barrier, made from Lexan, from polycarbonate, polyethylene, ABS, styrene acrylonitrile (SAN), poly-phenylene oxide (PPO), or other equivalent materials. Thus, by providing an original or starting occlusion configuration for the second port 46, longer storage life is made possible over similar containers and valves that have direct contact with an elastomeric membrane.

Figure 8:
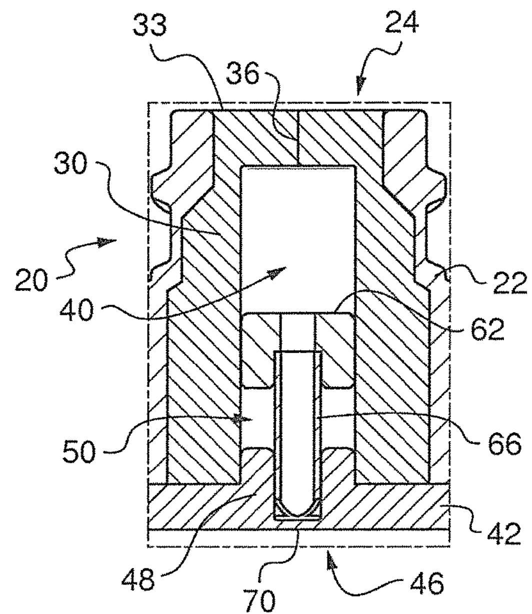
FIG. 8 shows a cross sectional view of a connector according to another proposed embodiment having a pierceable wall.

FIG. 8 shows a cross sectional view of the connector 20 in an alternative embodiment provided in accordance with the present device, system, and method. As shown, the c valve body 21 comprises a pierceable wall 70. The piereceable wall 70 may be unitarily formed with a second or lower valve body 42. As shown, the piereceable 70 wall forms the bottom of the well 48. The pierceable wall 70 occludes the second port 46 before the first activation and thus replaces the base portion 54 of the stem 50, previously described with reference to FIGS. 3 and 5-7. To pierce the pierceable wall 70 during a first activation, the stem 50 is modified to incorporate a sharpened end 66 located in the vicinity of the second port 46 and pointing away from the first port. On an opposite end of the stem 50, an abutment 62 is incorporated, which serves to transmit movement of the syringe tip inserted into the first port 26 to the sharpened end 66. As shown, the abutment 62 may have a sufficiently wide cap or head relative to the well 48 to limit the stem 50 from traveling completely through the well and exit the cavity 40 upon activation. One or more holes, channels, or ribs may be incorporated on the abutment 62 to provide flow paths in the event the abutment rests against the perimeter of the well.

Figure 9:
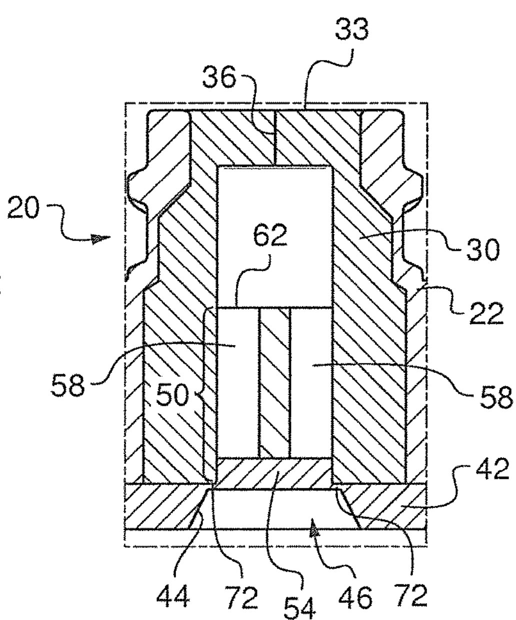
FIG. 9 shows a cross sectional view of a connector according to another proposed embodiment having a frangible portion integral with a stem disposed within the cavity of the hollow resilient membrane.

FIG. 9 shows a cross sectional view of the connector 20 according to another alternative embodiment of the present device, system, and method. The connector 20 is configured with a starting or original occlusion for isolating the membrane from fluids contained in the bag, receiver, or container. The isolation blocks the fluid path through the second port. In the present embodiment, the base portion 54 of the stem 50 is formed integrally with the valve body 21. In a specific embodiment, the base portion 54 is unitarily formed with the stem 50 and with the lower body portion 42. In another example, the base portion is unitarily formed with the lower body portion 42 only. As shown, the base portion 54 of the stem 50 is integrally formed with the valve body through a frangible portion 72. Here, the frangible portion 72 surrounds the base portion 54. Upon first activation, the stem 50 is pushed through the second port 46, causing the frangible portion 72 to rupture and the un-occluding the second port 46 thereby placing the contents of the bag or container in fluid communication with the interior cavity of the membrane 30. The stem 50 shown in FIG. 9 may incorporate several of the previously described features. For example, the stem 50 may have longitudinal ribs 58 as previously described. These ribs may form the previously described abutment 62. The stem 50 may also comprise a stop (not shown in FIG. 9) designed to abut against the well (not shown in FIG. 9) formed around the second hole 44.

Figure 10:
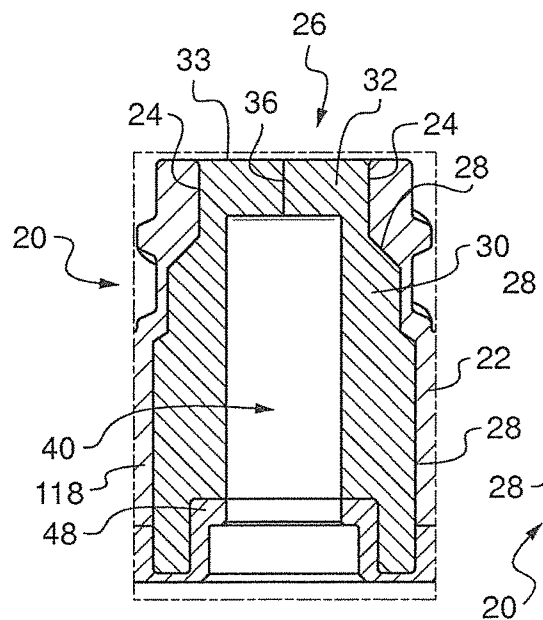
FIG. 10 shows a cross sectional view of a connector according to another proposed embodiment having a cylindrical hollow resilient membrane whose internal volume forms entirely a fluid passage.
Figure 11:
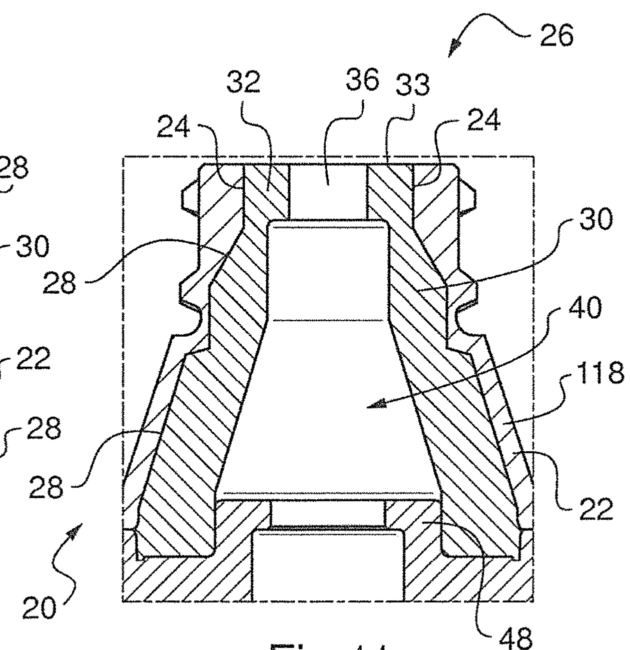
FIG. 11 shows a cross sectional view of a connector according to another proposed embodiment having a conical hollow resilient membrane whose internal volume forms entirely a fluid passage.

FIGS. 10 and 11 show cross sectional views of two additional alternative connectors provided in accordance with aspects of the present device, system, and method. FIG. 10 shows the connector 20 in a plane perpendicular to the extension plane of its slit 36, which is represented by a straight vertical line. FIG. 11 shows a connector 20 according to another embodiment in the plane of extension of its slit 36.

Referring again to FIG. 10, the connector 20 in accordance with aspects of the present device, system, and method includes the hollow resilient membrane 30 having the substantial portion of the flank 38 shaped in a cylindrical form or structure and defining an internal volume. However, the connector does not incorporate a stem and the internal cavity forms entirely a fluid passage. FIG. 11 shows the connector 20 with the hollow resilient membrane 30 having the substantial portion of the flank 38 shaped in a conical form and defining an internal volume. However, the connector does not incorporate a stem and the internal cavity forms entirely a fluid passage. Thus, for both embodiments of FIGS. 10 and 11, the cavity 40 of the membrane 30 does not include a stem or any other cannula.

Figure 12:
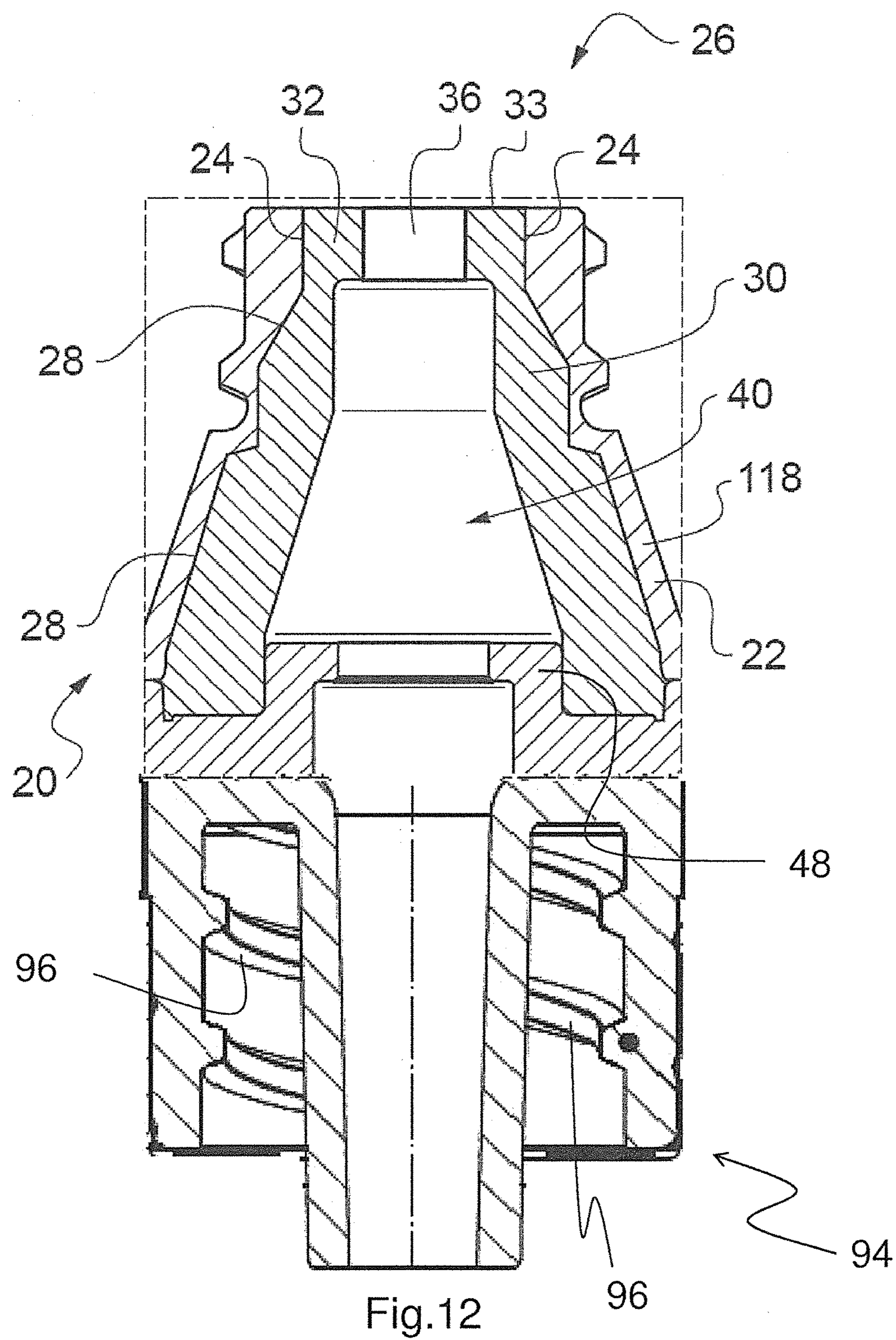
FIG. 12 shows a cross sectional view of a connector according to FIG. 11 together with a male luer lock outlet.

As a first consequence, the second port 46 of each connector 20 of FIGS. 10 and 11 is not originally occluded. Hence, these connectors may be used with an intravenous line or extension line. For such uses of the connector 20, initial occlusion of the second port to isolate the membrane of the connector and the drug recipient is not useful. Instead, a male luer fitting is typically provided at the second ports a male luer lock outlet, e.g. for the connection to intravenous line. FIG. 12 shows a cross sectional view of a connector according to FIG. 11 together with such a male luer lock outlet 94. According to this embodiment, the male luer may include a threaded shroud 96. The male luer lock outlet 94 is here distinct from the lower housing body 42, however in an alternative embodiment (not shown) the male luer lock outlet may form part of the lower housing body 42.

As a second consequence, when pushed or activated to provide fluid communication with a medical implement, the deformation of the first end 32 is not guided internally by any stem. For example, there is neither a sharpened end 60 nor a narrowing portion 64 of any stem 50 to facilitate opening and enlarging the slit 36 during activation of the first port 26. However, due to the close tolerance fit between the outer surface of the membrane and the internal surface of the valve body, as discussed above, deformation of the first end 32 may be guided by the internal surface 28 of the valve body to result in a reduction of the priming volume compared to similar connectors with outwardly expanding membranes. In one embodiment, the shape of the membrane 30 and the shape of the valve body 21 are configured so that the slit 36 of the first end 32 is forced closed when the first end 32 of the membrane is situated in the first port 26. For example, the annular space of the first port 26 could be sized to compress the first end 32 of the slit 36 to force the slit to close when the first end 32 of the membrane is located in the first port 26. When the first end 32 of the membrane is pressed by a syringe to force the first end 32 towards the second port 46, the membrane collapses and the slit 36 opens to permit fluid flow through the membrane. It is preferable that the size of the annular space or hole 24 of the first port 26 be chosen to compress the first end 32 to close the slit 36 and that the internal surface 28 of the valve body 21 includes an enlargement distal of the first hole 24 to permit expansion space for the slit. The provision of this enlargement is independent of the membrane shape or configuration (e.g. conical or cylindrical as illustrated in FIGS. 10 and 11).

In one embodiment, the slit 36 of the membrane 30 is normally opened when not located in the annular space of the first port, i.e. the first end 36 is hollow and the slit opens without external forces applied to the first end 32. For example, when the membrane is positioned outside the connector body, such as before installation, the slit opens in its normal unbiased state. Back to FIGS. 3 and 5 to 9, the slit of the membrane 30 may either embody a normally open slit 36 or a normally closed slit. According to the embodiment of the membrane with an normally open slit, by the time the slit engages the end 60 of the stem 50, the slit may be already partially opened and thus wraps around the end 60 of the stem 50 to further open. Preferably the slit 36 is normally closed, the slit 36 being formed through the membrane 30 with the use of a cutter.

In one embodiment when the first end 32 is located in the annular space of the first port 26, the top surface 33 of the first end 32 forms a flat swabbable surface with the connector body. Such a flat swabbable surface corresponds to a flat and smooth tip surface for the external face formed by the first end 32 together with the first port 26. Such a configuration presents a flat swabbable surface for cleaning and disinfecting. Thus, the connector may be easily cleaned before any connection with a luer lock syringe, resulting in a reduced contamination of fluids intended to be injected into a patient.

As above mentioned, the needle free connector is notably proposed for the use with a drug recipient, e.g., a mixing recipient, comprising a bottle, a bag or a container designed to store a drug. For such a use with a drug recipient, the proposed needle free connector may be assembled on the recipient. Accordingly, when the drug recipient is in the form of a bottle, the lower body part 42 of the needle free connector may be formed integral with or fixed to the bottle, e.g. either by sealing or by gluing, at an opening of the bottle. When the drug recipient is in the form of a bag having a flexible wall, the lower body part 42 may be fixed to or integral with a rigid base which is attached with the flexible wall to close the bag.

Figures 13, 14, 15:
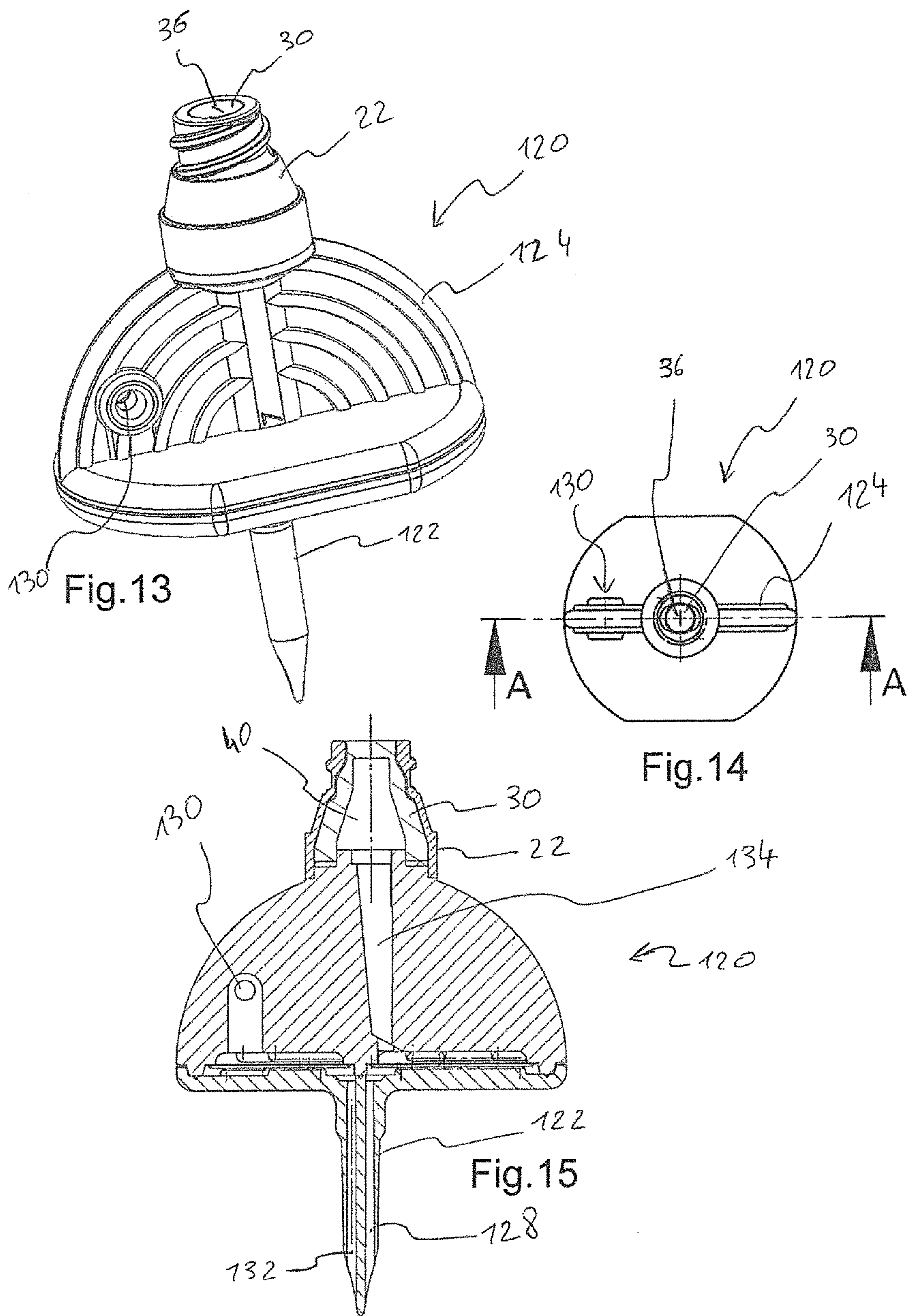
FIG. 13 shows a perspective view of a withdrawal and injection spike device incorporating a connector according to a proposed embodiment.
FIG. 14 shows a top view of the spike device according to FIG. 13.
FIG. 15 shows the cross sectional views A-A of FIG. 14.

Other uses of the proposed needle free connector may be envisaged in various embodiments of assemblies for fluid passage. FIG. 13 shows a perspective view of a spike device 120. This spike device 120 constitutes an envisaged embodiment of an assembly for fluid passage incorporating the proposed needle free connector 20. The membrane 30 is received in the cavity formed between the upper body portion 22 and a lower body portion 124. The lower body portion 124 is in the form of a flat grab handle. FIG. 14 shows a top view of the spike device 120. The proposed assembly in the form of a spike device 120 comprises a spike 122 for puncturing a drug vial. The spike may for example be used for puncturing a cap of the vial. Spike 122 comprises an internal canal for fluid passage once the device has punctured the vial, allowing the injection into and withdrawing from the vial of drug. With respect to FIG. 14, FIG. 15 shows the cross section A-A, illustrating the canal 128 formed in the spike 122. Canal 128 is connected to the internal cavity 40 of the membrane 30 thanks to a passage 134 formed in the flat grab handle 124. The spike device 120 having the proposed needle free connector 20, it allows to form, associated with a vial, a resealable vial from and into which drug can be withdrawn and injected without the use of a needle. For facilitating the withdrawing from and injection into the vial of drug, the flat grab handle may comprise an air inlet 130 connected to second canal 132 formed in the spike 122. The connection between the air inlet 130 and the second canal 132 could be provided with a filter (not shown). The above described spike device 120 preferably incorporates the embodiment of the proposed needle free connector 20 without initial occlusion of the second port 46 of the connector 20.

Figure 16:
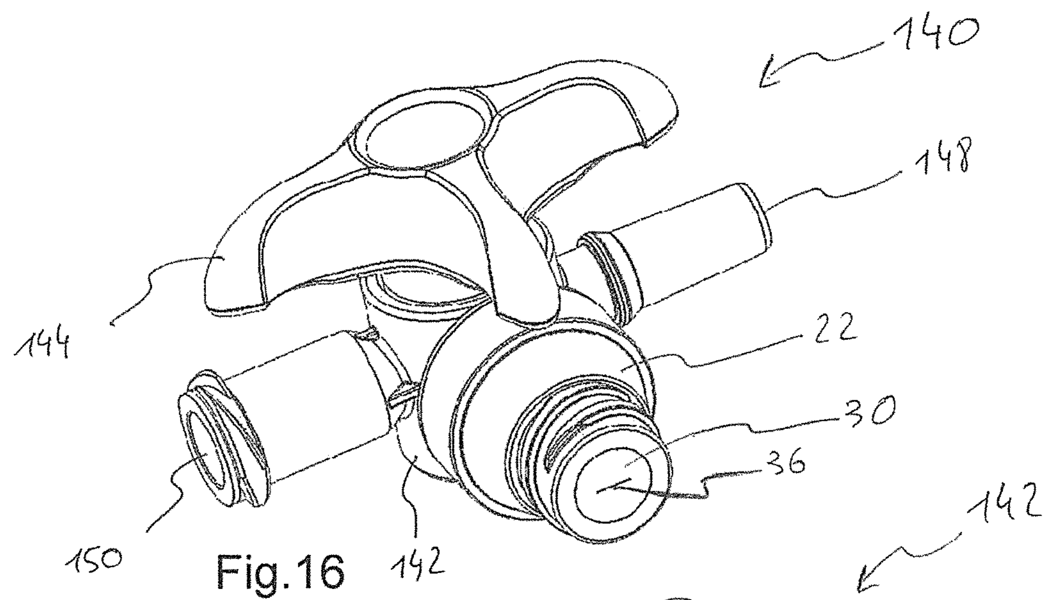
FIG. 16 shows a perspective view of a stopcock incorporating a connector according to a proposed embodiment.
Figure 17:
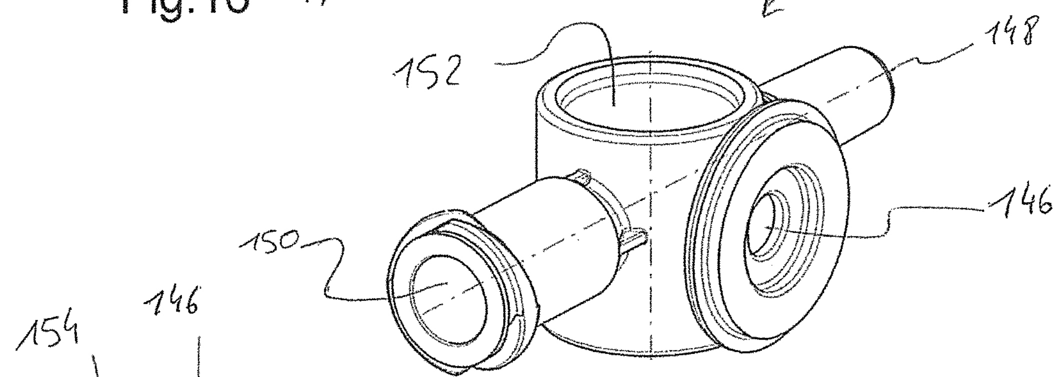
FIG. 17 shows a perspective view of the stopcock body alone of the stopcock according to FIG. 16.
Figure 18:
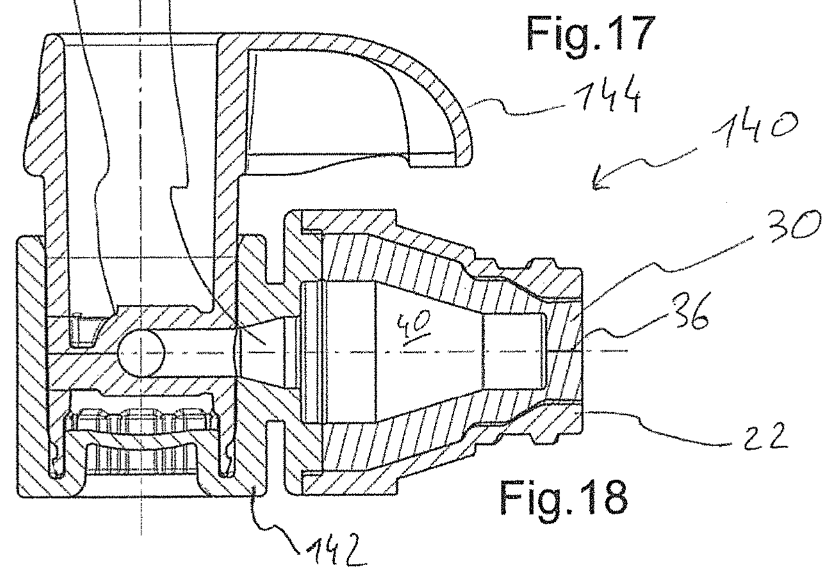
FIG. 18 shows a cross sectional view of the stopcock of FIG. 16 at the connector.

FIG. 16 shows a stopcock 140. This stopcock 140 constitutes an envisaged embodiment of an assembly for fluid passage incorporating the proposed needle free connector 20. The membrane 30 is received in the cavity formed between the upper body portion 22 and a lower body portion 142. The lower body portion 142 is in the form of a three way stopcock body. FIG. 17 shows a perspective view of the three way stopcock body 142 alone. The needle free connector is here disposed at the middle way 146 of the three way stopcock body. Alternatively, the needle free connector may be disposed at any of the other ways 148 or 150 of the stopcock body and/or the stopcock body may be a two way stopcock body (not shown). A right cylindrical hole 152 is provided for the reception of a plug of the stopcock and of a handle 144 controlling the orientation of the plug of the stopcock with respect to the three ways 146, 148 and 150. FIG. 18 shows a cross sectional view of the stopcock 140 in the radial plane of the hole 152 which bisects the way 146 on which the needle free connector is disposed. As illustrated the plug 154 is here positioned to allow flow passage between the way 146 and the other ways 148 and 150. The plug 154 is attached to the handle 144, e.g. by being integral with the handle 144. The above described stopcock 140 preferably incorporates the embodiment of the proposed needle free connector 20 without initial occlusion of the second port 46 of the connector 20.

In all the above described uses the drugs may either be an infusion liquid, or a medical liquid, or a nutritional liquid. The liquid may be in the form of solution.

Although limited embodiments of connectors and their components have been specifically described and illustrated herein, many modifications and variations will be apparent to those skilled in the art. For example, the various connectors may incorporate luer-slips rather than luer threads, the membrane the valve body or both may be made with different materials than described, and other surface features may be incorporated for aesthetic appeal. Furthermore, it is understood and contemplated that features specifically discussed for one connector may be adopted for inclusion with another connector provided the functions are compatible. For example, a pierceable membrane, as shown in FIG. 8, may be incorporated in the connector of FIG. 3. Accordingly, it is to be understood that the connectors and their components constructed according to principles of this invention may be embodied other than as specifically described herein. The invention is also defined in the following claims.

The invention claimed is:

1. A needle free connector for fluid passage, comprising:

a valve body comprising a first port, a second port, and an internal surface that extends between the first port and the second port and defining a valve body cavity;

a hollow resilient membrane disposed in the valve body, the hollow resilient membrane having a first end and a second end, the second end having a through hole that opens into the second port of the valve body, the hollow resilient membrane comprising a flank having an exterior surface and an interior surface extending between the first end and the second end and located in the valve body cavity of the valve body and fitting with the internal surface of the valve body, the flank defining an internal cavity of the hollow resilient membrane having an internal volume X when the first end is located at the first port, the internal cavity extending longitudinally from a through slit located at the first end to the through hole of the second end, the slit of the first end being closed when the first end is disposed in the first port so as to occlude the first port, the slit of the first end being opened when the first end is pushed into the valve body so as to create a fluid passage through the first end and the internal cavity of the flank up to the second end;

a stem disposed within the internal cavity of the flank having a tip and a base portion, said base portion occluding the second port of the valve body from through flow through the first port and the second port; and wherein all or parts of the exterior surface of the flank contacts the internal surface of the valve body such that a gap space between the internal surface of the valve body and the exterior surface of the hollow resilient membrane is fifteen percent or less of the internal volume X and such that the valve body outwardly delimits the flank of the hollow resilient membrane when opened;

wherein an internal volume of the hollow resilient membrane is smaller than the internal volume X when the first end of the hollow resilient membrane is located away from the first port;

wherein a first activation of the hollow resilient membrane in which the first end of the hollow resilient membrane is pushed away from the first port of the valve body also moves said base portion of said stem relative to said second port of the valve body to permanently separate said base portion from occluding said second port.

2. The needle free connector according to claim 1, wherein the first end of the hollow resilient membrane disposed in the first port forms a flat swabbable surface at the first port.

3. The needle free connector according to claim 1, wherein the stem has a base portion tight fitted with the second port until the first activation of the second port.

4. The needle free connector according to claim 1, wherein the stem has a base portion that occludes the second port and is integral with a valve body part of the valve body through a frangible portion until the first activation of the second port, the frangible portion being broken after the first activation of the second port.

5. The needle free connector according to claim 1, wherein the stem has longitudinal ribs forming fluid channels to keep the fluid passage between the stem and the flank of the hollow resilient membrane un-occluded upon activation of the first port.

6. The needle free connector according to claim 1, wherein the stem has a shoulder in the vicinity of the first port, designed to abut a tip of a syringe inserted in the first port upon first activation of the first port, so as to transmit the movement of the tip of the syringe to the stem and activate the second port.

7. The needle free connector according to claim 1, wherein the stem has a narrowing in a vicinity of the first port, designed to enter an inner channel of a tip of a syringe inserted in the first port.

8. A drug recipient comprising a bottle or a bag designed to store drug, and a needle free connector according to claim 1 so as to at least one of inject and withdraw fluid from the drug recipient.

9. An assembly for fluid passage comprising a needle free connector according to claim 1, the assembly being a stopcock or a withdrawal and injection spike device comprising a spike for puncturing a drug vial.

10. The needle free connector according to claim 1, wherein the gap space between the internal surface of the valve body and the external surface of the hollow resilient membrane is less than two percent of volume X to outwardly delimit the flank with the valve body when the first end of the hollow resilient membrane is opened.

11. The needle free connector according to claim 1, wherein the gap space between the internal surface of the valve body and the exterior surface of the hollow resilient membrane is five percent or less of the internal volume X to outwardly delimit the flank with the valve body.

12. The needle free connector according to claim 1, wherein the first port is shaped so as to connect with a male luer lock syringe.

13. The needle free connector according to claim 12, wherein:

the first end of the hollow resilient membrane is displaceable towards the second port by insertion of a syringe tip into the first port; and the hollow resilient membrane being formed so as to urge the first end of the hollow resilient membrane back into the first port after removal of the syringe tip from the first port.

14. A needle free connector comprising:

a valve body formed from an upper body part and a lower body part attached to the upper body part, the upper body part having an internal surface extending from a first port and the lower body part comprising a second port;

a hollow resilient membrane disposed inside the valve body, said hollow resilient membrane comprising a membrane body having an interior surface and an exterior surface, the interior surface defining an internal cavity extending longitudinally between a slit at a first end of the hollow resilient membrane to an opening at a second end of the hollow resilient membrane opposite the first end, the exterior surface comprising a membrane head, a lower membrane section, and a membrane shoulder located between the membrane head and the lower membrane section;

a stem disposed within the internal cavity of the membrane body and extending at least in part through the slit when the hollow resilient membrane is compressed;

wherein the membrane head, the membrane shoulder, and the lower membrane section contact the internal surface of the upper body part when the hollow resilient membrane is not compressed; and wherein when the hollow resilient membrane is compressed a first time, the membrane body is displaced inwardly towards the internal cavity to reduce a volume of the internal cavity of the membrane body and the stem is displaced from the internal cavity of the membrane body to permanently un-occlude the second port of the valve body from through flow through the first port and the second port.

15. The needle free connector of claim 14, wherein a gap space between the internal surface of the valve body and the exterior surface of the membrane body is fifteen percent or less of the volume of the internal cavity of the membrane body before the hollow resilient membrane is compressed.

16. The needle free connector of claim 14, wherein the stem has a narrowing portion at a distal end, and at least a portion of the narrowing portion extends through the slit when the hollow resilient membrane is compressed.

17. The needle free connector of claim 16, wherein the narrowing portion enters an inner channel of a tip of a syringe inserted in the first port, and the stem comprises a shoulder designed to abut and be pushed by the tip of the syringe.

18. The needle free connector of claim 17, wherein the shoulder is located proximal of the distal end.

19. The needle free connector of claim 17, wherein a stop is located proximal of the distal end and extends radially from the stem to limit the extent of movement of the stem.

20. A needle free connector comprising:

a valve body formed from an upper body part and a lower body part attached to the upper body part, the upper body part having an internal surface extending from a first port and the lower body part comprising a second port;

a hollow resilient membrane comprising a membrane body having an interior surface and an exterior surface, the interior surface defining an internal cavity extending longitudinally between a slit at a first end of the hollow resilient membrane to an opening at a second end of the hollow resilient membrane opposite the first end, the exterior surface comprising a membrane head, a lower membrane section, and a membrane shoulder located between the membrane head and the lower membrane section;

a movable stem disposed within the internal cavity of the membrane body and having a base portion, said base portion of the stem sealing against the valve body to form a barrier at a second port to separate all of the hollow resilient membrane from fluid communication with the second port prior to a first activation of the hollow resilient membrane; and wherein the membrane body is displaced inwardly towards the internal cavity when the hollow resilient membrane is compressed to reduce a volume of the internal cavity of the membrane body and to un-occlude the second port by moving the stem.

21. The needle free connector of claim 20, wherein the stem comprises a tip and wherein the tip projects through the slit at the first end of the hollow resilient membrane when the membrane body is displaced.

22. The needle free connector of claim 20, wherein the base portion is seal against an annular opening of the lower body part to occlude the second port from through flow through the first port and the second port.

* * * * *

UNITED STATES PATENT AND TRADEMARK OFFICE

CERTIFICATE OF CORRECTION

PATENT NO. : 9,724,270 B2
APPLICATION NO. : 14/236841
DATED : August 8, 2017
INVENTOR(S) : Olivier Bonnal and Juergen Fuchs It is certified that error appears in the above-identified patent and that said Letters Patent is hereby corrected as shown below:

On the Title Page

On the second page, in Column 2, in "Other Publications", Line 5, delete "Russia" and insert -- Russian --, therefor.

In the Specification

In Column 3, Line 48, delete "pierece" and insert -- pierce --, therefor.

In Column 8, Line 45, delete "silver sulfa diazine," and insert -- silver sulfadiazine, --, therefor.

In Column 9, Line 12, delete "stem, the stem, 50" and insert -- stem, the stem 50 --, therefor.

In Column 12, Lines 39-40, delete "piereceable" and insert -- pierceable --, therefor.

In Column 12, Line 41, delete "piereceable" and insert -- pierceable --, therefor.

Signed and Sealed this
Eleventh Day of December, 2018

Andrei Iancu
*Director of the United States Patent and Trademark Office*